United States Patent [19]

Janulis

[11] Patent Number: 5,095,142
[45] Date of Patent: Mar. 10, 1992

[54] SOLVENT RECOVERY DURING PRODUCTION OF AROMATIC POLYCARBOXYLIC ACIDS

[75] Inventor: Rose M. Janulis, Downers Grove, Ill.

[73] Assignee: Amoco Corporation, Chicago, Ill.

[21] Appl. No.: 620,154

[22] Filed: Nov. 29, 1990

[51] Int. Cl.$^5$ .............................................. C07C 51/265
[52] U.S. Cl. ..................................... 562/414; 562/416
[58] Field of Search .................................. 562/414, 416

[56] References Cited

U.S. PATENT DOCUMENTS

| | | | |
|---|---|---|---|
| 3,089,906 | 5/1963 | Saffer et al. | 562/414 |
| 3,089,907 | 5/1963 | Saffer et al. | 562/414 |
| 4,053,506 | 10/1977 | Park et al. | 562/414 |
| 4,855,492 | 8/1989 | Hundley | 562/414 |
| 4,877,900 | 10/1989 | Tamaru et al. | 562/413 |
| 5,004,830 | 4/1991 | Park et al. | 562/413 |

Primary Examiner—Jose G. Dees
Assistant Examiner—Vera C. Clarke
Attorney, Agent, or Firm—Gunar J. Blumberg; William H. Magidson; Ralph C. Medhurst

[57] ABSTRACT

A process for oxidizing a dialkyl substituted benzene, such as meta-xylene, to an aromatic polycarboxylic acid, such as isophthalic acid, in the presence of a solvent, such as acetic acid, in an oxidation zone followed by an oxidation-crystallization zone, wherein a secondary dehydration tower is used to separate water from the solvent in the overhead stream from the oxidation-crystallization zone and provide a solvent-rich fluid for recycle to the oxidation zone, resulting in expanded capacity of the process coupled with a minimization of captial cost.

24 Claims, 3 Drawing Sheets

SOLVENT RECOVERY DURING PRODUCTION OF AROMATIC POLYCARBOXYLIC ACIDS

BACKGROUND OF THE INVENTION

1. Field of the Invention

This present invention relates to processes for the oxidation of dialkyl substituted benzenes to aromatic polycarboxylic acids. More particularly, the present invention relates to an improved method for recovering solvent that is used in processes for the oxidation of dialkyl substituted benzenes to aromatic polycarboxylic acids.

2. Description of the Prior Art

The liquid-phase oxidation of a polyalkyl substituted benzene to an aromatic polycarboxylic acid is well known. Such processes are described by Saffer, et al, in U.S. Pat. Nos. 2,833,816, 3,089,906, and 3,089,907, and Park, et al, in U.S. Pat. No. 4,053,506.

As shown in the Park, et al, patent, the condensed vapors from the reaction zone may be sent to a distillation column, the solvent dehydration column, to dehydrate the monocarboxylic acid solvent that is used in the reaction zone. The water of reaction, as well as water added to the process for scrubbing vent streams must be removed from the monocarboxylic acid, i.e., acetic acid. This water removal is accomplished by distillation in the solvent dehydration column.

Oxygen-containing gas, e.g., air, may be introduced into the first crystallizer of the product recovery system of a process for the oxidation of a polyalkyl substituted benzene to an aromatic polycarboxylic acid. As a result, this first crystallizer becomes a combination oxidation-crystallization zone, wherein both crystallization of product and secondary oxidation of reactant occur. Vapor, containing water of reaction, is removed from this oxidation-crystallization zone and is sent to the solvent dehydration column. This vapor, along with the condensed liquid from the reaction zone, is treated in the solvent dehydration column. This vapor stream contains acetic acid, water, and inert gas comprising nitrogen, unreacted oxygen, and carbon oxides.

The capacity of the solvent dehydration column may be limiting the production rate of the polycarboxylic acid. Therefore the rate of the oxygen-containing gas to the oxidation-crystallization zone may not be at the level which is required or suitable for efficient operation of the oxidation-crystallization zone, since the resulting vapor stream, when combined with the condensed liquid obtained from the primary oxidation zone, would overtax the capacity of the solvent dehydration column. Consequently, the solvent dehydration step would become a bottleneck to increasing production rates at an existing unit.

The present invention removes this bottleneck by shifting part of the water removal from the solvent dehydration column to a new tower or column, identified hereinafter as the "secondary dehydration tower" or "secondary dehydration column".

SUMMARY OF THE INVENTION

According to the invention, there is provided a process for preparing an aromatic polycarboxylic acid wherein a dialkyl substituted benzene is oxidized to the aromatic polycarboxylic acid in a primary of first oxidation zone and the effluent comprising the polycarboxylic acid is sent to an oxidation-crystallization zone where secondary oxidation occurs, the overhead stream from the oxidation-crystallization zone is sent to a secondary dehydration column or tower wherein at least a portion of the water in this overhead stream is removed from the solvent contained therein.

In one embodiment, the overhead stream from the oxidation-crystallization zone is subjected to reboiling and stripping in the secondary dehydration column and the solvent-rich fluid from the secondary dehydration column is recycled to the first oxidation zone.

In a second embodiment, the overhead stream from the oxidation-crystallization zone is subjected to rectification only in the secondary dehydration column, and the solvent-rich fluid from the secondary dehydration column is sent to the solvent dehydration column.

In a third embodiment, the secondary dehydration column is designed for higher solvent concentration in the overhead condensate from that column, which increased solvent concentration will result in a reduction of the number of trays in the column.

In addition, the condensate from the overhead stream obtained from the secondary dehydration tower may be contacted in an absorber with off-gas from the overhead from the first oxidation zone to remove solvent from the off-gas and become enriched in solvent. The enriched condensate is then passed to a first dehydration tower wherein the increased solvent in the condensate from the secondary dehydration tower and that solvent recovered from the off-gas is recovered in the first dehydration tower.

BRIEF DESCRIPTION OF THE INVENTION

These FIGURES are simplified diagrams and, therefore, do not show various pieces of auxiliary equipment, such as pumps, compressors, heat exchangers, valves, and the like. However, one skilled in the art would recognize when such pieces would be used and where they would be located.

DETAILED DESCRIPTION AND PREFERRED EMBODIMENTS

The process of the present invention provides improved solvent recovery when a dialkyl substituted benzene is oxidized to an aromatic polycarboxylic acid and the effluent comprising the polycarboxylic acid from the primary or first oxidation zone is passed to an oxidation-crystaliization zone.

As shown hereinafter, a process for the oxidation of a dialkyl substituted benzene to an aromatic polycarboxylic acid may be conducted with an oxygen-containing gas, such as air, being introduced into the first crystallizer, as well as the reaction (oxidation) zone. This secondary oxidation improves yield, lowers solvent burning, and reduces catalyst requirements.

Unfortunately, the vapor stream from the first crystallizer is sent to the solvent dehydration tower. This stream contains water vaporized due to (1) the flash of reactor effluent to the first crystallizer pressure, (2) the heat of crystallization, and (3) the secondary oxidation heat of reaction. It contains also inert gas, which is composed of nitrogen, unreacted oxygen, and carbon oxides.

Solvent dehydration involves separating water from the monocarboxylic acid solvent and removing the water from the process by way of the overhead stream from the solvent dehydration tower. Inert gas enters the solvent dehydration tower via the vapor stream from the oxidation-crystallization zone and is vented to the atmosphere from the dehydration-tower reflux drum.

According to the present invention, there is provided a process for preparing an aromatic polycarboxylic acid by oxidizing a dialkyl substituted benzene, which process comprises introducing a first oxygen-containing gas, a feed stream comprising said dialkyl substituted benzene, a catalyst comprising a heavy metal catalyst and a source of bromine, and a solvent comprising an aliphatic monocarboxylic acid having from two to six carbon atoms into a first oxidation zone, converting at least a portion of said dialkyl substituted benzene to a first portion of said polycarboxylic acid at a temperature within the range of from about 120° C., preferably from about 150° C. (302° F.) to about 240° C. (482° F.) and a pressure that is sufficient to provide a liquid phase at said temperature in said first oxidation zone, withdrawing a first effluent comprising said first portion of said polycarboxylic acid from said first oxidation zone and passing said first effluent to an oxidation-crystallization zone, withdrawing a first overhead stream comprising water, solvent, and noncondensables from said first oxidation zone, separating said first overhead stream into a first condensate comprising water and solvent and a first off-gas comprising noncondensables, passing at least a portion of said first condensate to a first dehydration tower, separating a portion of the water in said first condensate from the solvent in said first condensate in said first dehydration tower to form a first solvent-rich fluid, withdrawing said first solvent-rich fluid from said first dehydration tower and passing said first solvent-rich fluid to said first oxidation zone, converting additional dialkyl substituted benzene, intermediates, or additional dialkyl substituted benzene and intermediates to a second portion of said polycarboxylic acid in the presence of a second oxygen-containing gas and crystallizing at least a part of said first portion of said polycarboxylic acid and said second portion of said polycarboxylic acid in said oxidation-crystallization zone to form in said oxidation-crystallization zone a second effluent comprising crystals of said polycarboxylic acid and a second overhead stream, withdrawing said second overhead stream from said oxidation-crystallization zone and passing said second overhead stream to a secondary dehydration tower, forming in said secondary dehydration tower a second solvent-rich fluid and a third overhead stream comprising water, solvent, and noncondensables, separating said third overhead stream into a second condensate comprising water and solvent and a second off-gas comprising noncondensables, passing said second solvent-rich fluid to said first oxidation zone, withdrawing said second effluent from said oxidation-crystallization zone, passing said second effluent to a product recovery zone, and recovering said polycarboxylic acid from said product recovery zone.

The term "solvent-rich fluid" as used herein means that the fluid contains less water than it did prior to the dehydration treatment of the fluid.

In this improved method, the improvement comprises passing said second overhead stream from said oxidation-crystallization zone to a secondary dehydration tower and forming said solvent-rich fluid in said secondary dehydration tower.

In one embodiment, the secondary dehydration tower is equipped with a cooler and condensate drum at the top of the tower to provide reflux to the tower and rectification, i.e., removal of solvent from water as the latter passes up through the upper portion of the tower, and a reboiler at the bottom of the tower to furnish reboiling and stripping in the lower portion of the tower, i.e., separation of the water from the solvent as the solvent descends down through the lower portion of the tower, and the solvent-rich stream being withdrawn from the secondary dehydration tower is passed to the first oxidation zone.

In another embodiment, the secondary dehydration tower is equipped only with a cooler and condensate drum at the top of the tower to provide reflux to the tower and rectification only and the solvent-rich stream being withdrawn from the secondary dehydration tower is passed to the first dehydration tower.

In another embodiment of the process of the present invention, at least a portion of the overhead condensate from the secondary dehydration tower is passed to an absorber where it contacts countercurrently the off-gas from the first oxidation zone to remove solvent from that off-gas and the solvent-enriched overhead condensate from the secondary dehydration tower then is sent to the first dehydration tower. In this particular embodiment, the secondary dehydration tower may be employed with either reboiling, stripping, and rectification or rectification only and may be designed for an increased solvent concentration in the overhead condensate.

According to the present invention, this embodiment, a preferred embodiment, is an improved process for preparing an aromatic polycarboxylic acid by oxidizing a dialkyl substituted benzene, which process comprises introducing a first oxygen-containing gas, a feed stream comprising said dialkyl substituted benzene, a catalyst comprising a heavy metal catalyst and a source of bromine, and a solvent comprising an aliphatic monocarboxylic acid having from two to six carbon atoms into a first oxidation zone, converting at least a portion of said dialkyl substituted benzene to a first portion of said polycarboxylic acid at a temperature within the range of about 150° C. (302° F.) to about 250° C. (482° F.) and a pressure that is sufficient to provide a liquid phase at said temperature in said first oxidation zone, withdrawing a first effluent comprising said first portion of said polycarboxylic acid from said first oxidation zone and passing said first effluent to an oxidation crystallization zone, withdrawing a first overhead stream comprising water, solvent, and non-condensables from said first oxidation zone, separating said first overhead stream into a first condensate comprising water and solvent and a first off-gas comprising noncondensables, passing at least a portion of said first condensate to a first dehydration tower, separating a portion of the water in said first condensate from the solvent in said first condensate in said first dehydration tower to form a first solvent-rich fluid, withdrawing said first solvent-rich fluid from said first dehydration tower and passing said first solvent-rich fluid to said first oxidation zone, converting additional dialkyl substituted benzene, intermediates, or additional dialkyl substituted benzene and intermediates to a second portion of said polycarboxylic acid in the presence of a second oxygen-containing gas and crystallizing at least a part of said polycarboxylic acid in said oxidation-crystallization zone to form a second effluent comprising crystals of said polycarboxylic acid and a second overhead stream, withdrawing said second overhead stream from said oxidation-crystallization zone and passing said second overhead stream to a secondary dehydration tower, forming in said secondary dehydration tower a second solvent-rich fluid and a third overhead stream comprising water, solvent, and noncondensables, withdrawing from said secondary dehydration tower said third overhead stream and separating said third overhead stream into a second condensate comprising water and solvent and a second off-gas comprising noncondensables, passing said second condensate to an absorber zone, contacting countercurrently in said absorber zone said second condensate with said first off-gas to form an absorber bottoms comprising said second condensate enriched with solvent from said first off-gas, passing said absorber bottoms to said first dehydration tower, withdrawing said second solvent-rich fluid from said second dehydration tower, passing said second solvent-rich fluid to said first oxidation zone, withdrawing said second effluent from said oxidation-crystallization zone, passing said second effluent to a product recovery zone, and recovering said polycarboxylic acid from said product recovery zone.

In this improved method, the improvement comprises passing said second overhead stream from said oxidation-crystallization zone to a secondary dehydration tower, forming in said secondary dehydration tower said second solvent-rich fluid and a third overhead stream, which may have a higher concentration of solvent than the overhead stream of the first dehydration tower, withdrawing from said secondary dehydration tower said third overhead stream and separating said third overhead stream into a second condensate comprising water and solvent and a second off-gas comprising noncondensables, passing said second condensate to an absorber zone, contacting countercurrently in said absorber zone said second condensate with said first off-gas to form an absorber bottoms comprising said second condensate enriched with solvent from said first off-gas, and passing said absorber bottoms to said first dehydration tower.

The addition of this secondary dehydration tower provides a means for overcoming the limitations resulting from insufficient capacity of the first dehydration tower at an existing unit. Such secondary dehydration tower can remove a portion of the water normally processed in the solvent dehydration tower and eliminate the inert gas from the solvent dehydration tower, i.e., the first dehydration tower. In this manner, the first dehydration tower is debottlenecked. The number of trays in the secondary dehydration tower can be minimized by designing for a higher solvent concentration in the overhead stream and by using the overhead distillate for reflux to the unit absorbers so that solvent is recovered in the absorber bottoms. The tray requirement of the secondary dehydration tower may be reduced significantly, if the tower is designed for a high solvent level in the overhead liquid, e.g., about 5 wt %.

The use of this liquid as absorber reflux will result in the solvent being recovered in the absorber bottoms.

It should be pointed out that the secondary dehydration tower having rectification only will furnish adequate debottlenecking of the first dehydration tower at minimum fixed capital investment.

Certain aromatic polycarboxylic acids may be prepared conveniently by the catalytic oxidation of alkyl-substituted aryl compounds via molecular oxygen. For example, para-xylene may be converted to terephthalic acid and meta-xylene may be converted to isophthalic acid.

Such oxidation is effected by reacting the alkyl-substituted aryl compound with molecular oxygen in the conjoint presence of catalytic amounts of a heavy metal catalyst and of bromine. The heavy metal catalyst comprises a member of the group consisting of manganese, cobalt, nickel, chromium, vanadium, molybdenum, tungsten, tin, cerium, and mixtures thereof. These metals, as well as others that have atomic numbers that are not greater than 84, are suitable for this oxidation catalyst and are presented in the "Periodic Chart of the Elements" on pages 58 and 59 of LANGE'S HANDBOOK OF CHEMISTRY, 6th edition, published by Handbook Publishers, Inc., Sandusky, Ohio, 1946. A preferred heavy metal catalyst comprises manganese and cobalt. The metal of the oxidation catalyst may be added in the elemental, combined, or ionic form. In addition, the bromine of the oxidation catalyst may be added in the elemental, combined, or ionic form. The metal or metals may be supplied in the form of metal salts of a lower aliphatic carboxylic acid, such as a metal acetate, in the form of an organic complex, such as an acetylacetonate, or as metal salts, such as the borates, halides, and nitrates. Bromine may be added as ionic bromine, such as ammonium bromide or other bromine compound that is soluble in the reaction medium. Potassium bromide, tetrabromoethane, and benzyl bromide are suitable sources of bromine.

The oxidation reaction is conducted at a temperature within the range of about 150° C. (302° F.) to about 250° C. (482° F.) and preferably within the range of about 170° C. (338° F.) to about 225° C. (437° F.). It is carried out under essentially liquid-phase conditions. The temperature and pressure should be so regulated as to provide a liquid phase in the reaction zone. Generally, the pressure is maintained within the range of atmospheric to about 1,500 psig (10,444 kPa).

When the effluent from the oxidation zone is passed to an oxidation-crystallization zone, the temperature in the latter zone is maintained within the range of about 138° C. (280° F.) to about 238° C. (460° F.), preferably within the range of about 154° C. (310° F.) to about 214° C. (417° F.).

The oxidation is carried out with an oxygen-containing gas as a source of molecular oxygen. The gas may be 100% oxygen or a gas mixture containing a lower concentration of oxygen, e.g., air.

The reaction time should be sufficiently long to enable a suitable conversion to result, i.e., about 0.5 to about 25 hours or more. A reaction time within the range of about 0.5 hour to about 2 hours is preferred.

Typically, oxygen is used in an amount to provide a mole ratio of about 2 moles of oxygen per mole of substituted aromatic material to about 500 moles of oxygen per mole of substituted aromatic material; desirably, within the range of about 5 to about 300 moles of oxygen per mole of substituted aromatic material; and preferably, within the range of about 5 to about 75 moles of oxygen per mole of substituted aromatic material.

The oxidation is a liquid-phase reaction. The liquid phase may comprise all or a portion of the organic reactant, or it may comprise a reaction medium in which the organic reactant is soluble or suspended. Such reaction medium may be added to facilitate carrying out the desired reaction or recovering desired product(s). This added reaction medium is suitably a monocarboxylic acid relatively stable or inert to oxidation in the reaction system. Typically, the monocarboxylic acid contains 2 to 6 carbon atoms, e.g., acetic acid.

Suitably, the reaction medium, if a lower aliphatic monocarboxylic acid, is used in an amount to provide a ratio of about 0.1 to about 10 parts by weight reaction medium per part of aromatic material, desirably a ratio of about 0.5 to about 4, and preferably a ratio of about 1 to about 2.5 parts by weight reaction medium per part of aromatic material.

In U.S. Pat. Nos. 2,833,816, 3,089,906, and 3,089,907, Saffer, et al, teach various embodiments of such oxidation processes. In U.S. Pat. No. 4,053,506, Park, et al, provide a process for producing terephthalic acid or isophthalic acid of fiber-grade quality.

The accompanying figures and following examples will facilitate a better understanding of the process of the present invention and are presented for the purpose of illustration only. They are not intended to limit the scope of the present invention.

Figure 1:
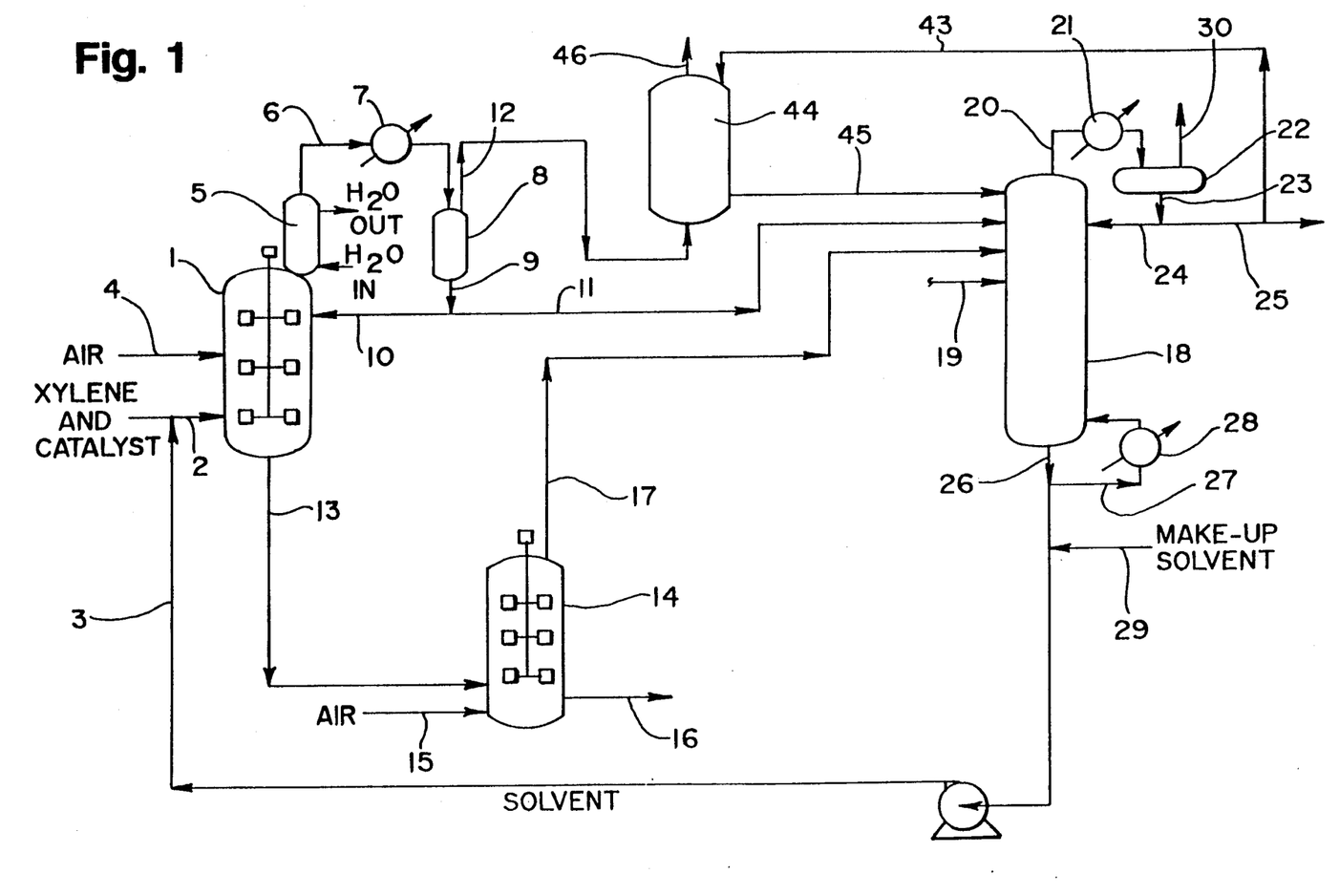
FIG. 1 presents a simplified schematic diagram of a process for the preparation of an aromatic polycarboxylic acid wherein secondary oxidation is conducted in an oxidation-crystallization zone or vessel.

FIG. 1 presents a simplified schematic diagram of a typical process for the preparation of an aromatic polycarboxylic acid wherein secondary oxidation is carried out in an oxidation-crystallization zone or vessel.

Referring to FIG. 1, the xylene feed comprising meta-xylene and catalyst are introduced into the primary oxidation (reaction) zone 1 through line 2 after the feed and catalyst have been combined with recycled solvent from line 3. An oxygen-containing gas, such as compressed air, is introduced into reaction zone 1 via line 4. The reaction mixture is stirred or agitated continuously in reaction zone 1, which may exist in the form of one or more reactors or stages. A portion of the reaction zone-overhead condensate, which is rich in water, is removed to control effectively the water concentration in the reaction zone 1. Vapors from the reaction zone 1 pass through one or more condensers 5. A large portion of the acetic acid solvent contained in the overhead vapor is condensed and removed as liquid reflux to reaction zone 1. Uncondensed vapors pass through line 6 and heat exchanger 7. Additional vapor is condensed and the condensate is collected in a secondary condenser pot 8. The condensate, which contains water and solvent, is withdrawn from condenser pot 8 through line 9 and may be split into two streams, so that a portion of the condensate may be passed to solvent recovery through line 12. The rest of the condensate is returned to reaction zone 1 via line 10. Any vapor remaining in condenser pot 8 is vented through line 12.

The oxidation catalyst system employed in this process scheme is similar to the ones described hereinabove, and the process conditions utilized in this process scheme fall within the ranges of values presented hereinabove.

The polycarboxylic acid, in this case, isophthalic acid, is removed from reaction zone 1 as oxidation effluent by way of line 13 and is sent to an oxidation-crystallization zone 14. A second oxygen-containing gas, e.g., compressed air, is introduced into oxidation-crystallization zone 14 via line 15. In oxidation-crystallization zone 14, a portion of the polycarboxylic acid is crystallized while additional xylene and/or intermediates are converted to the polycarboxylic acid. The effluent, a slurry containing crystals of the polycarboxylic acid, is removed from oxidation-crystallization zone 14 by way of line 16 and is passed to a second crystallizer, which is part of the product recovery system (not shown). The overhead from oxidation-crystallization zone 14 is withdrawn from oxidation-crystallization zone 14 by way of line 17 and passed to first dehydration zone (solvent dehydration zone) 18.

The condensate in line 11 and solvent obtained from the product recovery system in line 19, along with the overhead material from the oxidation-crystallization zone 14 in line 17, are charged to first dehydration zone or tower 18 for recovery of the solvent (acetic acid). Water-rich vapor is removed from tower 18 via line 20 through heat exchanger 21. The resulting condensate is collected in condensate drum 22. This condensate is removed from drum 22 through line 23 and is split into two streams, one of which passes through line 24 as reflux to column or tower 18 and one of which is removed in line 25, as discard.

Recovered solvent is withdrawn from column 18 through line 26. A portion of this material is passed through line 27 and reboiler 28 and reintroduced into the bottom of tower 18. Another portion of the recovered solvent in line 26 is combined with make-up solvent from line 29 and passed through line 3 to be combined with the xylene feed and catalyst in line 2. Any remaining vapor and noncondensables are vented from drum 22 via line 30.

Alternatively, at least a portion of the condensate in line 25 is passed via line 43 to an absorber zone 44 where it is contacted with first off-gas from line 12. Any solvent remaining in the first off-gas is removed by the condensate and then passed by way of line 45 to dehydration tower 18. Any remaining condensate in line 25 is sent to waste treatment. The stripped off-gas is vented from the absorber zone 45 via line 46.

Figures 2, 3:
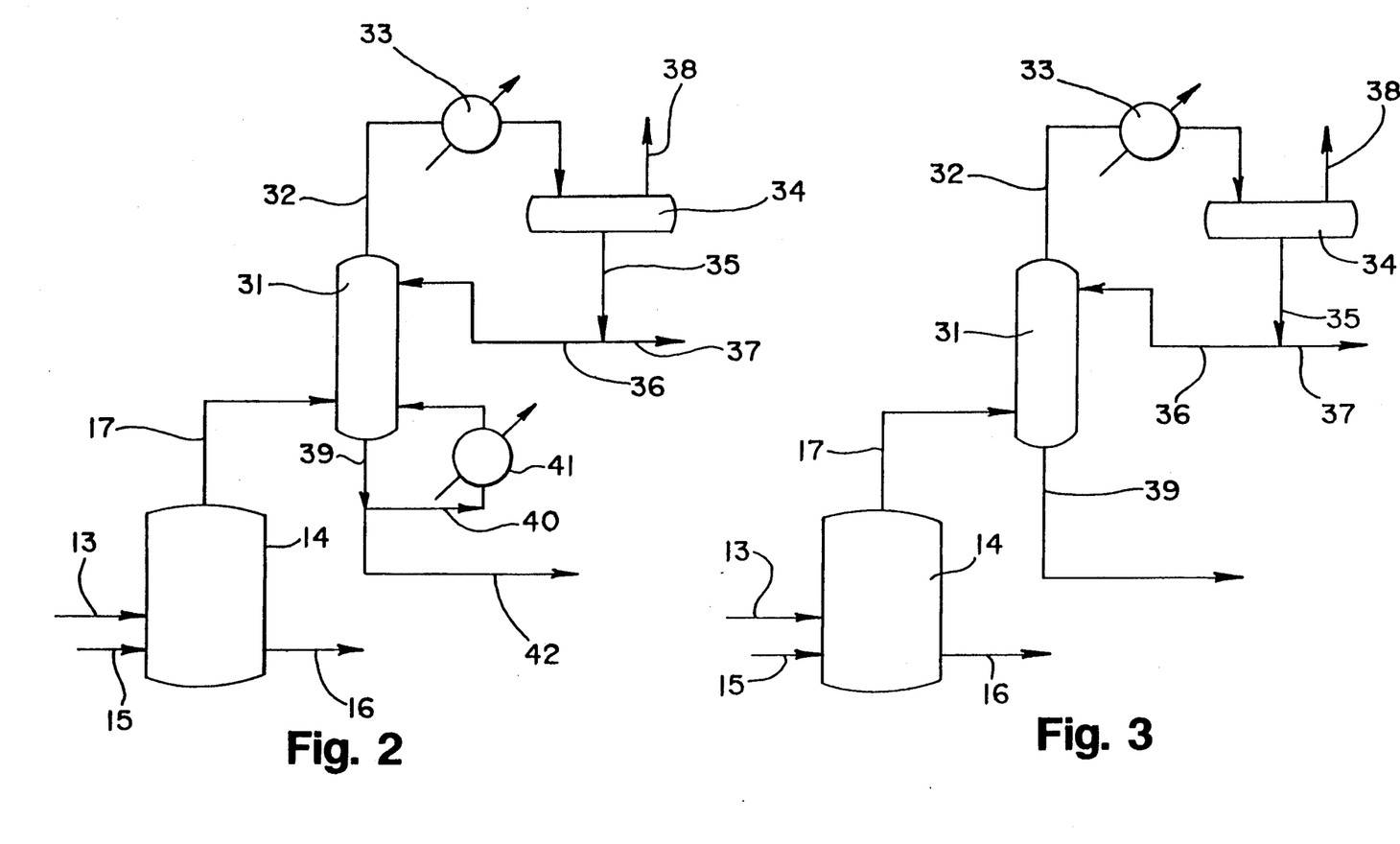
FIG. 2 provides a simplified diagram showing the oxidation-crystallization vessel and the secondary dehydration tower in one embodiment of the present invention.
FIG. 3 provides a simplified diagram depicting the oxidation-crystallization vessel and the secondary dehydration tower in a second embodiment of the present invention.

A first embodiment of the process of the present invention is depicted in FIG. 2, which shows the oxidation-crystallization zone 14 of the process of FIG. 1 and the modifications made to the process of FIG. 1.

Referring to FIG. 2, the reaction effluent from the first oxidation zone 1 of FIG. 1 is introduced into oxidation-crystallization zone 14 via line 13 and oxygen-containing gas is added via line 15. Crystallization of a portion of the polycarboxylic acid and some oxidation of xylene and/or intermediates occurs in oxidation-crystallization zone 14. The effluent, a slurry of polycarboxylic acid crystals, is withdrawn from zone 14 via line 16 and is sent to the second crystallizer, which is part of the product recovery system (not shown). The overhead from oxidation-crystallization zone 14 is withdrawn therefrom via line 17 and is passed to second dehydration tower 31. A water-rich stream is removed as overhead via line 32. This stream is passed through line 32 and heat exchanger 33 into condensate drum 34. The noncondensables and any remaining vapor are separated from the condensate, which is withdrawn from drum 34 by way of line 35. A portion of the condensate in line 35 is returned to second dehydration tower 31 by way of line 36, while the remainder is withdrawn via line 37 to waste treatment or absorbers (not shown). The solvent-rich bottoms stream is withdrawn from second dehydration tower 31 via line 39. A portion of this stream is passed through line 40 and reboiler 41 and returned to the bottom of tower 31. The remainder of the solvent-rich stream is passed through line 42 to the first oxidation zone.

In this embodiment, reboiling, stripping, and rectification take place in the second dehydration tower 31.

A second embodiment of the process of the present invention is represented in FIG. 3.

Referring to FIG. 3, the scheme is similar to that shown in FIG. 2, with the exception that no reboiler is present. The solvent-rich stream is recovered from the second dehydration tower 31 by way of line 39 and is sent to the first dehydration zone or tower 18 (shown in FIG. 1) by way of line 39.

In this second embodiment, only rectification takes place in the second dehydration tower 31.

Figure 4:
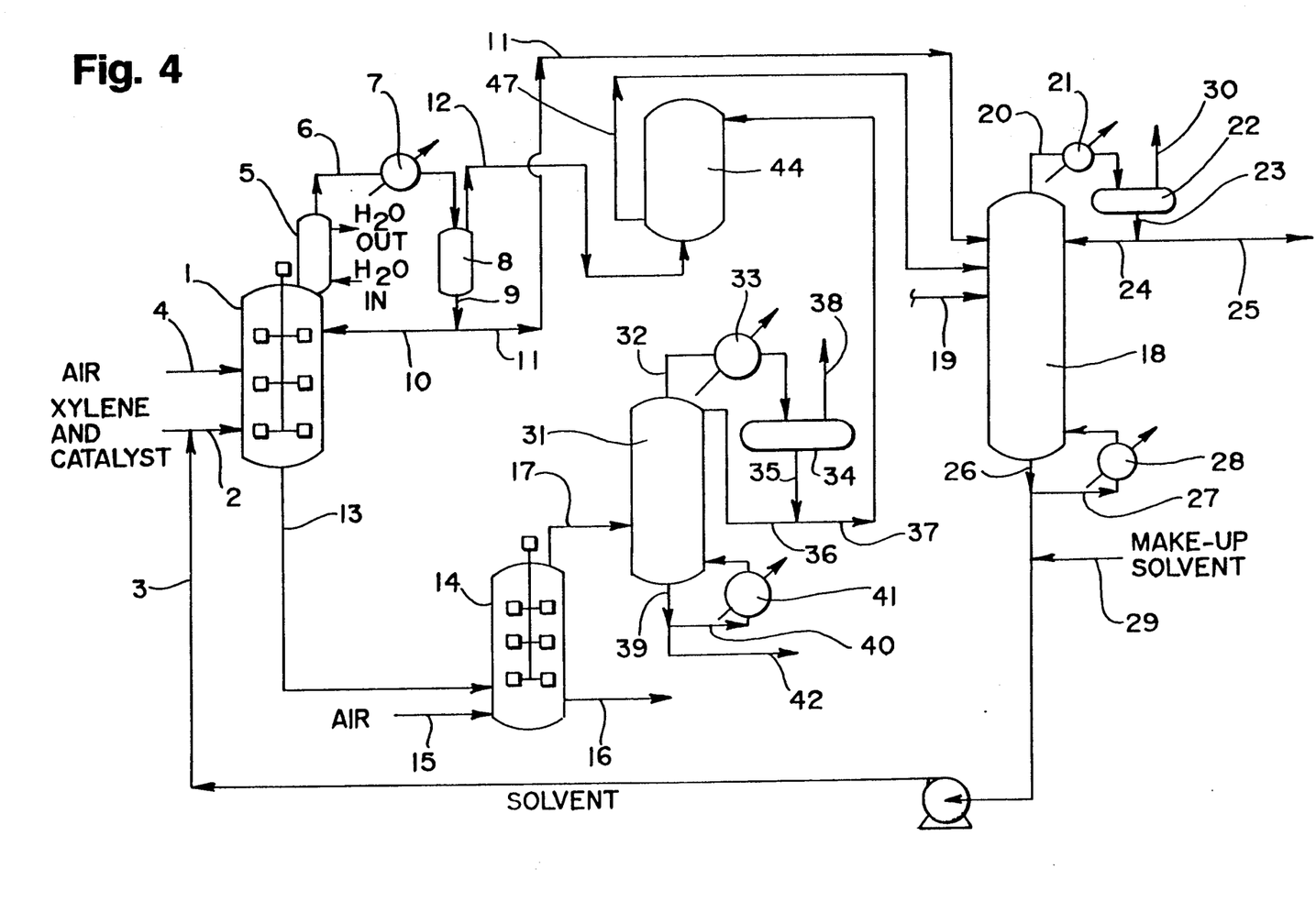
FIG. 4 provides a simplified schematic diagram presenting the process represented by FIG. 1 when employing the scheme presented in FIG. 2.

FIG. 4 presents a simplified schematic diagram of a preferred embodiment of the process of the present invention.

Referring to FIG. 4, the xylene feed comprising meta-xylene and catalyst are introduced into a first oxidation zone 1 through line 2 after the feed and catalyst have been combined with recycled solvent from line 3. An oxygen-containing gas, such as air, is introduced into oxidation zone 1 via line 4. The reaction mixture is stirred or agitated continuously in oxidation zone 1, which may exist in the form of one or more reactors or stages. A portion of the oxidation zone-overhead condensate, which is rich in water, may be removed to control effectively the water concentration in the reaction or oxidation zone 1. Vapors from the oxidation zone 1 pass through one or more condensers 5. A large portion of the solvent, acetic acid, contained in the overhead vapor is condensed and removed as liquid reflux to oxidation zone 1. Uncondensed vapors pass through line 6 and heat exchanger 7. Additional vapor is condensed and the condensate is collected in a secondary condenser pot 8. The condensate, which contains water and solvent, is withdrawn from condenser pot 8 through line 9 and may be split into two streams. A portion of the condensate may be passed to a first dehydration tower through line 11. The rest of the condensate is returned to oxidation zone 1 via line 10. Any vapor remaining in condenser pot 8 is vented through line 12.

The oxidation catalyst system and the process conditions that are employed in this process scheme are the same as those discussed hereinabove.

Isophthalic acid, the polycarboxylic acid produced, is withdrawn from oxidation zone 1 via line 13 and is transferred to oxidation-crystallization zone 14. Compressed air or other oxygen-containing gas is introduced into oxidation-crystallization zone 14 via line 15. At least a portion of the isophthalic acid is crystallized and additional meta-xylene and/or intermediates are converted to the polycarboxylic acid. A slurry comprising crystals of isophthalic acid is removed from oxidation-crystallization zone 14 by way of line 16 and is passed via line 16 to a crystallizer, which is part of a product recovery system (not shown). Overhead is withdrawn from oxidation-crystallization zone 14 via line 17 and is passed to secondary dehydration tower 31.

The condensate in line 11 and solvent obtained from the product recovery system in line 19, along with the solvent-enriched condensate obtained from absorber 44 in line 47 as described hereinafter, are charged to first dehydration zone or tower 18 for recovery of the solvent (acetic acid). Water-rich vapor is removed from tower 18 via line 20 through heat exchanger 21. The resulting condensate is collected in condensate drum 22. This condensate is removed from drum 22 through line 23 and is divided into two streams, one of which passes through line 24 as reflux to tower 18 and one of which is removed via line 25 as discard.

Recovered solvent is withdrawn from tower 18 through line 26. A portion of this material is passed through line 27 and reboiler 28 and returned to the bottom of tower 18. A second portion of the recovered solvent in line 26 is combined with make-up solvent from line 29 and passed through line 3 to be combined with the xylene feed and catalyst in line 2. Any remaining vapor and noncondensables are vented from drum 22 via line 30.

The second overhead is withdrawn from oxidation crystallization zone 14 via line 17 and is passed to secondary dehydration tower 31. A water-rich stream is separated from the overhead from the oxidation-crystallization zone 14 in second dehydration tower 31 and is withdrawn from tower 31 as overhead by way of line 32. This stream is passed through line 32 and heat exchanger 33 into condensate drum 34. The noncondensables and any remaining vapor are separated from the condensate, which is withdrawn from drum 34 by way of line 35. A portion of the condensate in line 35 is returned to secondary dehydration tower 31 via line 36, while the remainder is removed by way of line 37. Off-gas is removed from condensate drum 34 via line 38.

The solvent-rich bottoms stream is withdrawn from secondary dehydration tower 31 via line 39. A portion of this stream is passed through line 40 and reboiler 41 and returned to the bottom of tower 31. The remainder of this solvent-rich stream is passed through line 42 to the first oxidation zone 1. This solvent-rich stream may be combined with the solvent in line 3.

The condensate from drum 34 in line 37 is passed through line 37 into the top of absorber 44 where it is contacted countercurrently with off-gas from secondary condenser pot 8, which is fed into the bottom of absorber 44 via line 12. Any solvent being carried in the off-gas is stripped therefrom by the condensate passing through absorber 44. This condensate enriched by the solvent from the off-gas is passed from absorber 44 through line 47 to first dehydration tower 18, wherein solvent is separated from water to be returned through lines 26 and 3 to the first oxidation zone 1. In this embodiment, the tray requirement in the secondary dehydration tower 31 is reduced and/or minimized by using a high-solvent level in the overhead liquid that is obtained from tower 31 and condensate drum 34, e.g., about 5 wt %.

The manner of treating the vapor stream from the oxidation-crystallization zone was studied in the following examples. In Example I, the vapor stream was sent to a secondary dehydration column equipped with a reboiler and an overhead condensation reflux system. In Example II, the vapor stream was sent to a secondary dehydration column equipped only with an overhead condensation reflux system.

In Example III, a 20-tray secondary dehydration tower was contemplated for use at a 5 wt % acetic acid level in the overhead condensate, which was used as absorber reflux.

The results in the following examples were obtained by calculations. A computer simulation of the oxidation zone and oxidation-crystallization zone was used to calculate the vapor stream obtained from the oxidation-crystallization zone. In these examples, a feed stream comprising meta-xylene was being oxidized to isophthalic acid. The solvent was acetic acid.

Computer simulations were written for: (1) the oxidation-crystallization zone separating tower having a liquid solvent concentration in the overhead in the 1.0 to 5.0 wt % range; (2) the solvent dehydration column; and (3) the high-pressure absorber. The simulations of the solvent dehydration tower and the high-pressure absorber were used as a convenient way to calculate differences in acetic acid loss and reboiler heat duty in order to compare the system having the secondary dehydration tower to the system that does not have the secondary dehydration tower.

The Example I and Example II secondary dehydration tower simulations examined the reflux rate versus tray requirement for a specified concentration of acetic acid in the overhead product. The simulations were run specifying an overhead product of all vapor. The overhead vapor product stream was flashed at 49° C. (120° F.) to find the liquid and vapor streams' compositions, assuming that the tower condenser would have an outlet temperature of 49° C. (120° F.).

For the reboiled tower, the flow rate of the bottoms product in moles per hr and the mole fraction of acetic acid in the overhead vapor were specified. The reflux rate was found by the computer simulation. The specifications were set to give a 9 wt % water bottoms product. For Example II, the rectification only tower being used therein, the reboiler duty was set to zero and the mole fraction of acetic acid in the overhead product (assuming a vapor product) was specified. The reflux rate and the flow rates of the overhead and bottoms products were determined by the program.

The calculated vapor stream from the oxidation-crystallization zone is presented hereinafter in Table I.

TABLE I

| COMPOSITION OF CALCULATED VAPOR STREAM FROM THE OXIDATION-CRYSTALLIZATION ZONE | |
|---|---|
| | mol/hr |
| Acetic Acid | 256.6 |
| Water | 298.2 |
| Inert Gas | 94.1 |
| Total | 648.9 |
| Temperature | 356° F. |
| Pressure | 115 psia |

EXAMPLE I

In this example, the secondary dehydration tower was equipped with a reboiler.

Table II provides the simulated relationship between the acetic acid concentration in the overhead vapor, number of trays, and reflux rate. The feed-tray location was found to be important, since the simulation for many of the tower designs would fail as a result of poor feed-tray location.

TABLE II

| SECOND DEHYDRATION TOWER WITH REBOILER | | | |
|---|---|---|---|
| No. of Theoretical Stages | Reflux Rate, mol/hr | Reboiler Duty, MMBtu/hr | Feed Tray |
| Case I: Overhead Liquid 5.05 wt % Acetic Acid | | | |
| 15 | 1485.6 | 20.99 | 14 |
| 20 | 843.9 | 9.58 | 18 |
| 25 | 730.3 | 7.57 | 20 |
| 30 | 671.3 | 6.54 | 22 |
| Case II: Overhead Liquid 2.5 wt % Acetic Acid | | | |
| 20 | 1295.2 | 17.61 | 19 |
| 25 | 880.9 | 10.24 | 24 |
| 30 | 735.6 | 7.66 | 28 |
| Case III: Overhead Liquid 1.0 wt % Acetic Acid | | | |
| 25 | 1911.4 | 28.6 | 20 |
| 30 | 1082.5 | 13.9 | 28 |

The high reboiler heat duties in Table II are a result of the difficulty of the acetic acid-water separation. The lower the acetic acid in the overhead stream, the more difficult is the separation. If 5 wt % acetic acid is specified in the overhead liquid stream, an easier separation is obtained. Compared to the 2.5 wt % acetic acid concentration, a 25-tray tower has a 26% lower reboiler duty.

The vapor stream coming from the oxidation-crystallization zone contains a major portion of the water that would be fed to the first dehydration tower. When a secondary dehydration tower with a reboiler is installed there is a reduction in the first dehydration tower overhead product rate from 499.5 moles per hr to 187.7 moles per hour and the vapor loading is reduced accordingly. Bottoms product rate is lowered by about 46% from 724.5 moles per hr to 387.8 moles per hr. Reboiler duty is lowered by 45%, with a difference of 7.1 MMBtu per hr.

EXAMPLE II

In this example, the secondary dehydration tower provides rectification only. It is not equipped with a reboiler.

Table III presents a summary of the simulations in this example. Assuming a vapor product, the acetic acid mole fraction in the overhead product was specified. The computer program found the required reflux rate, which determined the flow rates of the product streams. The composition of both product streams could not be set, since there was no stripping section.

The required tower diameter was about the same in all cases in this example. Vapor loading was set essentially by the feed stream.

The tray versus reflux rate relationships for various overhead liquid compositions are presented hereinafter in Table III. For example, for a 2 wt % acetic acid overhead liquid, a 15-tray tower has a reflux rate of 478 moles per hr and sends 4,889 lbs per hr of water to the solvent or first dehydration tower, whereas for approximately the same overhead liquid composition, a 30-tray tower requires about 400 moles per hr of reflux and sends 3,236 lb per hr of water to the first dehydration tower. Providing more trays in the secondary dehydration tower allows a greater reduction in the first-dehydration-tower overhead loss of acetic acid and reboiler duty.

TABLE III

| SECONDARY DEHYDRATION TOWER WITH RECTIFICATION ONLY | | | | |
|---|---|---|---|---|
| Reflux Rate, mol/hr | Overhead, Liquid | | Bottoms, Liquid | |
| | wt % HAc[1] | lb/hr | wt % H$_2$O | lb/hr |
| Case I: 15 Theoretical Trays | | | | |
| 477.9 | 2.0 | 276 | 24.1 | 20286 |
| 455.2 | 3.4 | 932 | 21.7 | 19631 |
| 437.0 | 4.9 | 1367 | 20.1 | 19196 |

TABLE III-continued
SECONDARY DEHYDRATION TOWER WITH RECTIFICATION ONLY

| Reflux Rate, | Overhead, Liquid | | Bottoms, Liquid | |
|---|---|---|---|---|
| mol/hr | wt % HAc[1] | lb/hr | wt % H$_2$O | lb/hr |
| 416.4 | 7.3 | 1856 | 18.4 | 18706 |
| Case II: 20 Theoretical Trays | | | | |
| 458.6 | 1.2 | 733 | 22.3 | 19831 |
| 428.9 | 2.5 | 1385 | 19.9 | 19180 |
| 420.4 | 3.3 | 1615 | 19.0 | 18950 |
| 403.7 | 4.9 | 1990 | 17.6 | 18574 |
| Case III: 30 Theoretical Trays | | | | |
| 400.7 | 2.2 | 1967 | 17.4 | 18601 |
| 391.7 | 4.5 | 2473 | 15.5 | 18094 |
| 369.4 | 6.0 | 2679 | 14.8 | 17887 |

[1]HAc = acetic acid

If the secondary dehydration tower has rectification only, there is provided flexibility in the reduction of the feed rate to the solvent dehydration tower. A dilute solvent stream is sent to the solvent dehydration tower, when the secondary dehydration tower provides rectification only. All of the inert gas and only the desired amount of water can be eliminated from the solvent dehydration tower.

If the secondary dehydration tower is equipped with a reboiler, the entire vapor stream from the oxidation-crystallization zone is eliminated from the solvent dehydration tower.

EXAMPLE III

In this example, an overhead liquid stream from the secondary dehydration tower was considered for use as absorber reflux. A 5 wt % acetic acid concentration was assumed for the overhead condensate. This higher acetic acid level allows the tray requirement in the secondary dehydration tower to be reduced.

To produce approximately the same bottoms stream, specifically a 5 wt % acetic acid concentration in the overhead condensate from the secondary dehydration tower requires 20 trays, while a 1.5 wt % acetic acid level needs 32 trays. A tower with 20 theoretical trays provides sufficient overhead liquid for absorber reflux and minimizes the capital cost for increasing the solvent dehydration capacity of the process.

With the secondary dehydration tower installed the operation of the first dehydration tower can be optimized for the lowest operating cost which is made up of energy usage in the reboiler and acetic acid lost in the overhead stream. For example, it may be possible to reduce the concentration of acetic acid in the first dehydration tower overhead by operating at a higher reflux ratio. In addition, with the secondary dehydration tower installed the air rate to the secondary-oxidation crystallization zone may be increased thereby allowing an optimization of the first and secondary oxidation zones in order to maximize yield, lower solvent burning, and reduce usage of catalyst in the reaction zones.

What is claimed is:

1. A process for preparing an aromatic polycarboxylic acid by oxidizing a dialkyl substituted benzene, which process comprises introducing a first oxygen-containing gas, a feed stream comprising said dialkyl substituted benzene, a catalyst comprising a heavy metal catalyst and a source of bromine, and a solvent comprising an aliphatic monocarboxylic acid having from two to six carbon atoms into a first oxidation zone, converting at least a portion of said dialkyl substituted benzene to a first portion of said polycarboxylic acid at a temperature within the range of about 150° C. to about 250° C. and a pressure that is sufficient to provide a liquid phase at said temperature in said first oxidation zone, withdrawing a first effluent comprising said first portion of said polycarboxylic acid from said first oxidation zone and passing said first effluent to an oxidation-crystallization zone, withdrawing a first overhead stream comprising water, solvent, and noncondensables from said first oxidation zone, separating said first overhead stream into a first condensate comprising water and solvent and a first off-gas comprising noncondensables, passing at least a portion of said first condensate to a first dehydration tower, separating a portion of the water in said first condensate from the solvent in said first condensate in said first dehydration tower to form a first solvent-rich fluid, withdrawing said first solvent-rich fluid from said first dehydration tower and passing said first solvent-rich fluid to said first oxidation zone, converting additional dialkyl substituted benzene, intermediates, or additional dialkyl substituted benzene and intermediates to a second portion of said polycarboxylic acid in the presence of a second oxygen-containing gas and crystallizing at least a part of said first portion of said polycarboxylic acid and said second portion of said polycarboxylic acid in said oxidation-crystallization zone to form in said oxidation-crystallization zone a second effluent comprising crystals of said polycarboxylic acid and a second overhead stream, withdrawing said second overhead stream from said oxidation-crystallization zone and passing said second overhead stream to a secondary dehydration tower, forming in said secondary dehydration tower a second solvent-rich fluid and a third overhead stream comprising water, solvent, and noncondensables, separating said third overhead stream into a second condensate comprising water and solvent and a second off-gas comprising noncondensables, passing said second solvent-rich fluid to said first oxidation zone, withdrawing said second effluent from said oxidation-crystallization zone, passing said second effluent to a product purification and recovery zone, and recovering said polycarboxylic acid from said product purification and recovery zone.

2. The process of claim 1, wherein said secondary dehydration tower provides reboiling, stripping, and rectification.

3. The process of claim 1, wherein said secondary dehydration tower provides rectification only.

4. A process for preparing an aromatic polycarboxylic acid by oxidizing a dialkyl substituted benzene, which process comprises introducing a first oxygen-containing gas, a feed stream comprising said dialkyl substituted benzene, a catalyst comprising a heavy metal catalyst and a source of bromine, and a solvent comprising an aliphatic monocarboxylic acid having from two to six carbon atoms into a first oxidation zone, converting at least a portion of said dialkyl substituted benzene to a first portion of said polycarboxylic acid at a temperature within the range of about 150° C. to about 250° C. and a pressure that issufficient to provide a liquid phase at said temperature in said first oxidation zone, withdrawing a first effluent comprising said first portion of said polycarboxylic acid from said first oxidation zone and passing said first effluent to an oxidation-crystallization zone, withdrawing a first overhead stream comprising water, solvent, and noncondensables from said first oxidation zone, separating said first overhead stream into a first condensate comprising water and solvent and a first off-gas comprising noncondensables, passing at least a portion of said first condensate to a first dehydration tower, separating a portion of the water in said first condensate from the solvent in said first condensate in said first dehydration tower to form a first solvent-rich fluid, withdrawing said first solvent-rich fluid from said first dehydration tower and passing said first solvent-rich fluid to said first oxidation zone, converting additional dialkyl substituted benzene, intermediates, or additional dialkyl substituted benzene and intermediates to a second portion of said polycarboxylic acid in the presence of a second oxygen-containing gas and crystallizing at least a part of said polycarboxylic acid in said oxidation-crystallization zone to form a second effluent comprising crystals of said polycarboxylic acid and a second overhead stream, withdrawing said second overhead stream from said oxidation-crystallization zone and passing said second overhead stream to a secondary dehydration tower, forming in said secondary dehydration tower a second solvent-rich fluid and a third overhead stream comprising water, solvent, and noncondensables, withdrawing from said secondary dehydration tower said third overhead stream and separating said third overhead stream into a second condensate comprising water and solvent and a second off-gas comprising noncondensables, passing said second condensate to an absorber zone, contacting countercurrently in said absorber zone said second condensate with said first off-gas to form an absorber bottoms comprising said second condensate enriched with solvent from said first off-gas, passing said absorber bottoms to said first dehydration tower, withdrawing said second solvent-rich fluid from said second dehydration tower, passing said second solvent-rich fluid to said first oxidation zone, withdrawing said second effluent from said oxidation-crystallization zone, passing said second effluent to a product purification and recovery zone, and recovering said polycarboxylic acid from said product purification and recovery zone.

5. The process of claim 4, wherein said secondary dehydration tower provides reboiling, stripping, and rectification.

6. The process of claim 4, wherein said secondary dehydration tower provides rectification only.

7. The process of claim 4, wherein said dialkyl substituted benzene is para-xylene and said aromatic polycarboxylic acid is terephthalic acid.

8. The process of claim 4, wherein said dialkyl substituted benzene is meta-xylene and said aromatic polycarboxylic acid is isophthalic acid.

9. The process of claim 5, wherein said dialkyl substituted benzene is para-xylene and said aromatic polycarboxylic acid is terephthalic acid.

10. The process of claim 5, wherein said dialkyl substituted benzene is meta-xylene and said aromatic polycarboxylic acid is isophthalic acid.

11. The process of claim 6, wherein said dialkyl substituted benzene is para-xylene and said aromatic polycarboxylic acid is terephthalic acid.

12. The process of claim 6, wherein said dialkyl substituted benzene is meta-xylene and said aromatic polycarboxylic acid is isophthalic acid.

13. In an improved process for the oxidation of a dialkyl substituted benzene to an aromatic polycarboxylic acid, wherein a feed stock comprising said dialkyl substituted benzene is contacted in a first oxidation zone with a catalyst comprising a heavy metal catalyst and a source of bromine in the presence of a first oxygen-containing gas and a solvent comprising an aliphatic monocarboxylic acid having from two to six carbon atoms, at least a portion of said dialkyl substituted benzene is converted in said first oxidation zone to a first portion of said polycarboxylic acid to form a first effluent comprising said first portion of said polycarboxylic acid and a first overhead stream, said first effluent is passed from said first oxidation zone to an oxidation-crystallization zone, said first overhead stream is separated into a first condensate comprising water and solvent and an off-gas comprising noncondensables, said first condensate is passed to a first dehydration tower to form a first solvent-rich fluid, additional dialkyl substituted benzene, intermediates, or additional dialkyl substituted benzene and intermediates are converted to a second portion of said polycarboxylic acid in the presence of a second oxygen-containing gas and at least a part of said first portion of said polycarboxylic acid and said second portion of said polycarboxylic acid is crystallized in said oxidation-crystallization zone to form a second effluent comprising polycarboxylic acid crystals and a second overhead stream comprising water, solvent, and noncondensables, said second overhead stream is withdrawn from said oxidation-crystallization zone and is treated to form a second solvent-rich fluid, said second effluent having suspended therein said crystals is withdrawn from said oxidation-crystallization zone and is passed to a product recovery zone, said first solvent-rich fluid and said second solvent-rich fluid are sent to said first oxidation zone, and said polycarboxylic acid crystals are recovered from said product recovery zone, the improvement which comprises passing said second overhead stream from said oxidation-crystallization zone to a secondary dehydration tower and forming said second solvent-rich fluid in said secondary dehydration tower.

14. The process of claim 13, wherein said secondary dehydration tower provides reboiling, stripping, and rectification and said second solvent-rich fluid is withdrawn from said secondary dehydration tower for transfer to said first oxidation zone.

15. The process of claim 13, wherein said secondary dehydration tower provides rectification only and said second solvent-rich fluid is withdrawn from said secondary dehydration tower and is sent to said first dehydration tower where additional water is removed from said second solvent-rich fluid prior to said second solvent-rich fluid being sent to said first oxidation zone.

16. The process of claim 14, wherein said second solvent-rich fluid is combined with said first solvent-rich fluid to form a combined solvent-rich fluid and said combined solvent-rich fluid is sent to said first oxidation zone.

17. In an improved process for the oxidation of a dialkyl substituted benzene to an aromatic polycarboxylic acid, wherein a feed stock comprising said dialkyl substituted benzene is contacted in a first oxidation zone with a catalyst comprising a heavy metal catalyst and a source of bromine in the presence of a first oxygen-containing gas and a solvent comprising an aliphatic monocarboxylic acid having from two to six carbon atoms, at least a portion of said dialkyl substituted benzene is converted in said first oxidation zone to a first portion of said polycarboxylic acid to form a first effluent comprising said first portion of said polycarboxylic acid and a first overhead steam, said first effluent is passed from said first oxidation zone to an oxidation-crystallization zone, said first overhead stream is separated into a first condensate comprising water and solvent and an off-gas comprising noncondensables, said first condensate is passed to a first dehydration tower to form a first solvent-rich fluid, additional dialkyl substituted benzene, intermediates or additional dialkyl substituted benzene and intermediates are converted to a second portion of said polycarboxylic acid in the presence of a second oxygen-containing gas and at least a part of said first portion of said polycarboxylic acid and said second portion of said polycarboxylic acid is crystallized in said oxidation-crystallization zone to form a second effluent comprising polycarboxylic acid crystals and a second overhead stream comprising water, solvent, and noncondensables, said second overhead stream is withdrawn from said oxidation-crystallization zone and is treated to form a second solvent-rich fluid, said second effluent having suspended therein said crystals is withdrawn from said oxidation-crystallization zone and is passed to a product purification and recovery zone, said first solvent-rich fluid and said second solvent-rich fluid are sent to said first oxidation zone, and said polycarboxylic acid crystals are recovered from said product purification and recovery zone, the improvement which comprises passing said second overhead stream from said oxidation-crystallization zone to a secondary dehydration tower, forming in said secondary dehydration tower said second solvent-rich fluid and a third overhead stream, withdrawing from said secondary dehydration tower said third overhead stream and separating said third overhead stream into a second condensate comprising water and solvent and a second off-gas comprising noncondensables, passing said second condensate to an absorber zone, contacting countercurrently in said absorber zone said second condensate with said first off-gas to form an absorber bottoms comprising said second condensate enriched with solvent from said first off-gas, and passing said absorber bottoms to said first dehydration tower.

18. The process of claim 17, wherein said secondary dehydration tower provides reboiling, stripping, and rectification and said second solvent-rich fluid is withdrawn from said secondary dehydration tower for transfer to said first oxidation zone.

19. The process of claim 17, wherein said secondary dehydration tower provides rectification only and said second solvent-rich fluid is withdrawn from said secondary dehydration tower and is sent to said first dehydration tower where additional water is removed from said second solvent-rich fluid prior to said second solvent-rich fluid being sent to said first oxidation zone.

20. The process of claim 18, wherein said second solvent-rich fluid is combined with said first solvent-rich fluid to form a combined solvent-rich fluid and said combined solvent-rich fluid is sent to said first oxidation zone.

21. In an improved process for the oxidation of meta-xylene to isophthalic acid wherein a feed stock comprising said meta-xylene is contacted with a catalyst comprising a heavy metal catalyst and a source of bromine in the presence of a first oxygen-containing gas and a solvent comprising acetic acid in a first oxidation zone, at least a portion of said meta-xylene is converted in said first oxidation zone, to a first portion of said isophthalic acid to form a first effluent comprising said first portion of said isophthalic acid and a first overhead stream, said first effluent is passed from said first oxidation zone to an oxidation-crystallization zone, said first overhead stream is separated into a first condensate comprising water and solvent and an off-gas comprising noncondensables, said first condensate is passed to a first dehydration tower to form a first acetic acid-rich fluid, additional meta-xylene, intermediates, or meta-xylene and intermediates are converted to a second portion of said isophthalic acid in the presence of a second oxygen-containing gas and at least a part of said first portion of said isophthalic acid and said second portion of said isophthalic acid is crystallized in said oxidation-crystallization zone to form a second effluent comprising isophthalic acid crystals and a second overhead stream comprising water, acetic acid, and noncondensables, said second overhead stream is withdrawn from said oxidation-crystallization zone and is treated to form a second acetic acid-rich fluid, said second effluent having suspended therein said crystals is withdrawn from said oxidation-crystallization zone and is passed to a product recovery zone, said first acetic acid-rich fluid and said second acetic acid-rich fluid are sent to said first oxidaton zone, and said isophthalic acid crystals are recovered from said product recovery zone, the improvement which comprises passing said second overhead stream from said oxidation-crystallization zone to a secondary dehydration tower, forming in said secondary dehydration tower said second acetic acid-rich fluid and a third overhead stream, withdrawing from said secondary dehydration tower said third overhead stream and separating said third overhead stream into a second condensate comprising water and acetic acid and a second off-gas comprising noncondensables, passing said second condensate to an absorber zone, contacting countercurrently in said absorber zone said second condensate with said first off-gas to form an absorber bottoms comprising said second condensate enriched with acetic acid from said first off-gas, and passing said absorber bottoms to said first dehydration tower.

22. The process of claim 21, wherein said secondary dehydration tower provides reboiling, stripping, and rectification and said second acetic acid-rich fluid is withdrawn from said secondary dehydration tower for transfer to said first oxidation zone.

23. The process of claim 21, wherein said secondary dehydration tower provides rectification only and said second acetic acid-rich fluid is withdrawn from said secondary dehydration tower and is sent to said first dehydration tower where additional water is removed from said second acetic acid-rich fluid prior to said second acetic acid-rich fluid being sent to said first oxidation zone.

24. The process of claim 22, wherein said second acetic acid-rich fluid is combined with said first acetic acid-rich fluid to form a combined acetic acid-rich fluid and said combined acetic acid-rich fluid is sent to said first oxidation zone.

* * * * *

UNITED STATES PATENT AND TRADEMARK OFFICE
CERTIFICATE OF CORRECTION

PATENT NO. : 5,095,142
DATED : March 10, 1992
INVENTOR(S) : Rose M. Janulis

It is certified that error appears in the above-indentified patent and that said Letters Patent is hereby corrected as shown below:

Col. 12, line 57-58, "in the first-dehydration" should read -- in the first-dehydration--.

Column 14, line 60, "that issufficient" should read --that is sufficient --.

Column 16, line 66, "overhead steam" should read --overhead stream--.

Signed and Sealed this

Twenty-sixth Day of October, 1993

Attest:

BRUCE LEHMAN

*Attesting Officer*     *Commissioner of Patents and Trademarks*